United States Patent
Feine

(10) Patent No.: US 10,020,679 B2
(45) Date of Patent: *Jul. 10, 2018

(54) HANDHELD ELECTRICAL DEVICE SYSTEM AND METHOD

(71) Applicant: James Feine, Bellaire, TX (US)

(72) Inventor: James Feine, Bellaire, TX (US)

( * ) Notice: Subject to any disclaimer, the term of this patent is extended or adjusted under 35 U.S.C. 154(b) by 148 days.

This patent is subject to a terminal disclaimer.

(21) Appl. No.: 14/717,406

(22) Filed: May 20, 2015

(65) Prior Publication Data

US 2015/0333535 A1    Nov. 19, 2015

Related U.S. Application Data

(63) Continuation-in-part of application No. 13/456,051, filed on Apr. 25, 2012, now Pat. No. 9,050,161.
(Continued)

(51) Int. Cl.
*A61C 1/07* (2006.01)
*H02J 50/10* (2016.01)
(Continued)

(52) U.S. Cl.
CPC ............ *H02J 50/10* (2016.02); *A61B 5/4547* (2013.01); *A61C 1/0015* (2013.01); *A61C 17/20* (2013.01);
(Continued)

(58) Field of Classification Search
CPC ...... H02J 5/005; A61B 5/4547; A61B 5/0075; A61B 5/0088; A61B 2506/0214;
(Continued)

(56) References Cited

U.S. PATENT DOCUMENTS

| | | | |
|---|---|---|---|
| 3,634,742 A | * | 1/1972 | Edson ..................... H01L 41/12 310/26 |
| 4,012,647 A | | 3/1977 | Balamuth et al. |
| | | | (Continued) |

FOREIGN PATENT DOCUMENTS

| | | |
|---|---|---|
| DE | 3708801 | 9/1988 |
| EP | 1182984 | 3/2002 |
| | (Continued) | |

OTHER PUBLICATIONS

U.S. Appl. No. 60/806,807, filed Jul. 11, 2006, Bollig et al., 25 pages.
PCT/US07/84953; ISR and WO, dated Apr. 18, 2008.

*Primary Examiner* — Heidi M Eide
(74) *Attorney, Agent, or Firm* — Daniel N. Lundeen; Lundeen & Lundeen PLLC

(57) ABSTRACT

An apparatus and a handheld electrical tool system comprising an insert receivable in an ultrasonic handpiece comprising a primary coil disposed about a well and electrically connected to a primary current supply, the insert comprising a secondary coil disposed about at least a portion of the insert dimensioned and arranged to be disposable within the well such that the secondary coil is inductively coupled to the primary coil, the secondary coil in electrical communication with at least one electrical device powered by the secondary coil. A method of operating a handpiece and of retrofitting a handpiece is also disclosed.

17 Claims, 11 Drawing Sheets

Related U.S. Application Data

(60) Provisional application No. 61/483,479, filed on May 6, 2011, provisional application No. 61/480,685, filed on Apr. 29, 2011.

(51) Int. Cl.
  *H01F 38/14* (2006.01)
  *A61C 17/20* (2006.01)
  *A61C 1/00* (2006.01)
  *A61B 5/00* (2006.01)
  *A61C 1/08* (2006.01)

(52) U.S. Cl.
  CPC ............ *H01F 38/14* (2013.01); *A61B 5/0075* (2013.01); *A61B 5/0088* (2013.01); *A61B 2560/0214* (2013.01); *A61B 2562/0271* (2013.01); *A61C 1/07* (2013.01); *A61C 1/088* (2013.01)

(58) Field of Classification Search
  CPC . A61B 2562/0271; A61C 1/0015; A61C 1/07; A61C 1/088; A61C 17/20; H01F 38/14
  See application file for complete search history.

(56) References Cited

U.S. PATENT DOCUMENTS

| | | |
|---|---|---|
| 4,283,175 A | 8/1981 | Nash |
| 4,578,033 A | 3/1986 | Mossle et al. |
| 4,820,152 A * | 4/1989 | Warrin ................. A61C 17/20 219/643 |
| 5,059,122 A | 10/1991 | Hetzel |
| 5,423,677 A | 6/1995 | Brattesani |
| 5,538,423 A | 7/1996 | Coss et al. |
| 5,730,594 A | 3/1998 | Sharp |
| 5,754,016 A | 5/1998 | Jovanovic et al. |
| 5,868,563 A | 2/1999 | Davis et al. |
| 5,899,692 A | 5/1999 | Davis et al. |
| 6,029,304 A | 2/2000 | Hulke et al. |
| 6,164,968 A | 12/2000 | Feine |
| 6,208,788 B1 | 3/2001 | Nosov |
| 6,312,256 B1 | 11/2001 | Dieras et al. |
| 6,328,566 B1 | 12/2001 | Feine |
| 6,386,866 B1 | 5/2002 | Hecht et al. |
| 6,470,222 B1 | 10/2002 | Davidson et al. |
| 6,503,081 B1 | 1/2003 | Feine |
| 6,666,860 B1 | 12/2003 | Takahashi |
| 6,899,538 B2 | 5/2005 | Matoba |
| 6,976,843 B2 | 12/2005 | Feine |
| 7,104,792 B2 | 9/2006 | Levy |
| 7,150,629 B2 | 12/2006 | Feine |
| 7,473,097 B2 | 1/2009 | Raby et al. |
| 7,614,878 B2 | 11/2009 | Paschke et al. |
| 7,761,174 B2 | 7/2010 | Nyholm |
| 7,766,656 B1 | 7/2010 | Feine |
| 8,204,612 B2 | 6/2012 | Feine et al. |
| 2002/0072035 A1 | 6/2002 | Hickok |
| 2003/0115694 A1 | 6/2003 | Pace |
| 2004/0092991 A1 | 5/2004 | Deng |
| 2004/0255409 A1 | 12/2004 | Hilscher et al. |
| 2006/0074405 A1 | 4/2006 | Malackowski et al. |
| 2006/0281044 A1 | 12/2006 | Case et al. |
| 2007/0011836 A1* | 1/2007 | Brewer ............... A46B 15/0002 15/220.1 |
| 2007/0244581 A1 | 10/2007 | Nyholm |
| 2007/0254262 A1 | 11/2007 | Doussin et al. |
| 2008/0064006 A1* | 3/2008 | Quan .................... A61C 1/0015 433/119 |
| 2008/0145817 A1 | 6/2008 | Brennan et al. |
| 2008/0193893 A1 | 8/2008 | Beck |
| 2008/0293008 A1 | 11/2008 | Regere et al. |
| 2009/0162810 A1 | 6/2009 | Werner et al. |
| 2009/0202961 A1* | 8/2009 | Fani ....................... A61C 1/088 433/119 |
| 2009/0226856 A1 | 9/2009 | Sauter et al. |
| 2010/0036535 A1 | 2/2010 | Feine |
| 2010/0092913 A1 | 4/2010 | Andell et al. |
| 2011/0033823 A1 | 2/2011 | Gersh et al. |
| 2011/0183283 A1 | 7/2011 | Strassl et al. |
| 2013/0096468 A1* | 4/2013 | Rhee ............... A61B 17/320092 601/2 |

FOREIGN PATENT DOCUMENTS

| | | |
|---|---|---|
| EP | 1480570 | 12/2004 |
| FR | 2871677 | 12/2005 |
| WO | 9905984 | 2/1999 |
| WO | 2008008782 | 1/2008 |
| WO | 20090117464 | 9/2009 |
| WO | 2010139762 | 12/2010 |
| WO | 2010146228 | 12/2010 |

* cited by examiner

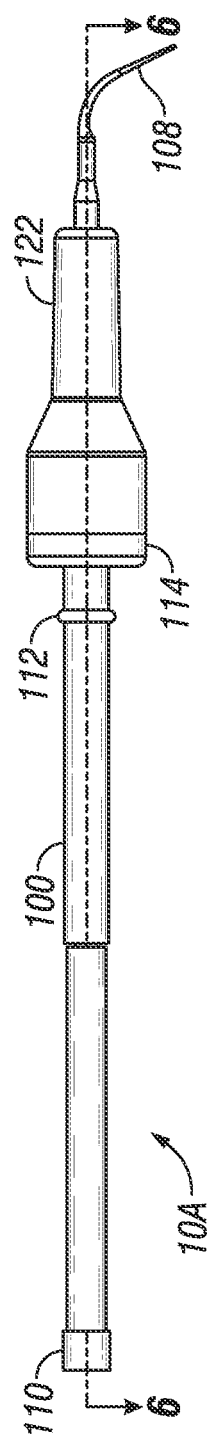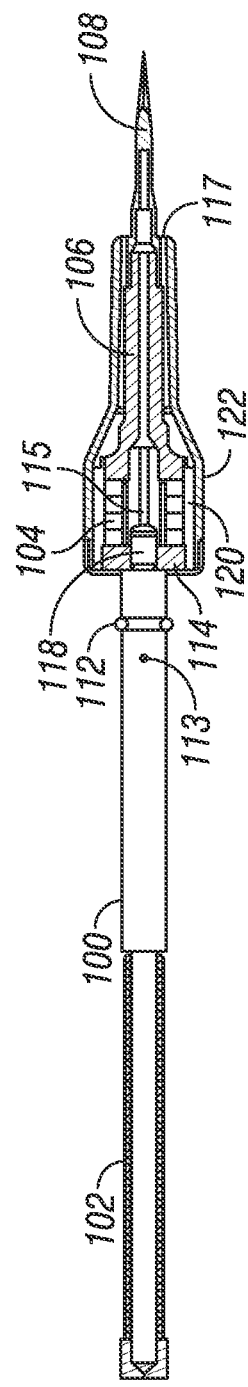

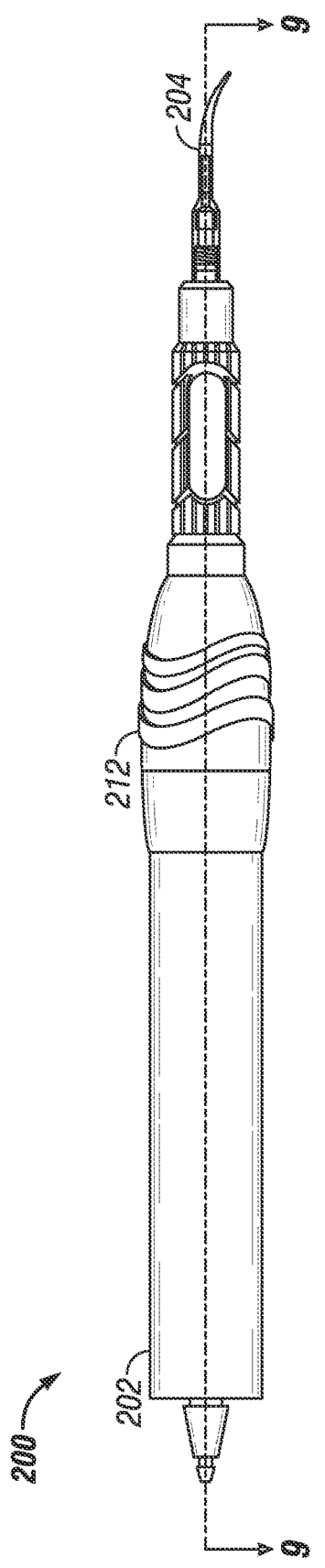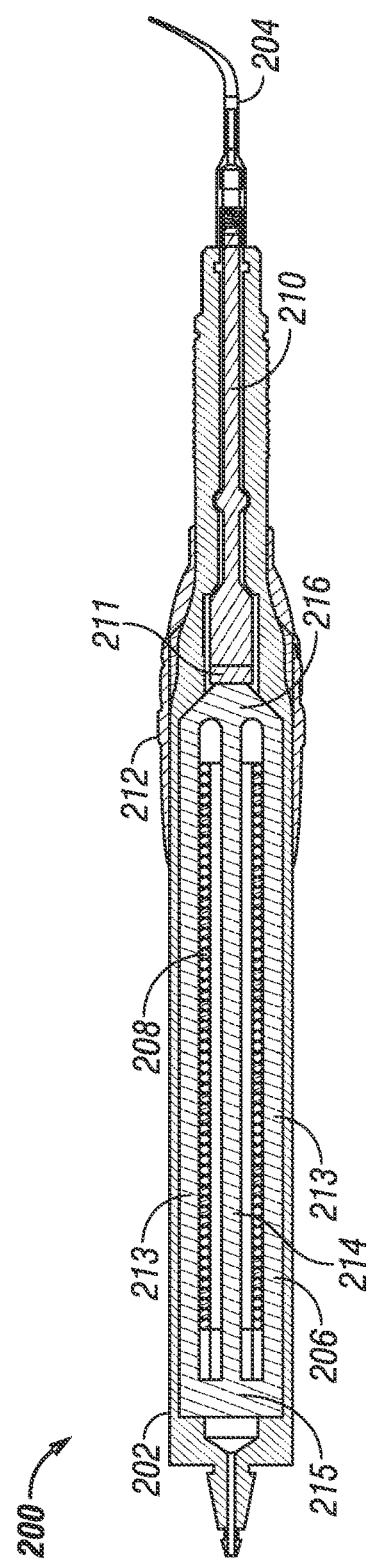

HANDHELD ELECTRICAL DEVICE SYSTEM AND METHOD

CROSS REFERENCE TO RELATED APPLICATIONS

This application is a continuation-in-part of U.S. Ser. No. 13/456,051, filed Apr. 25, 2012, now U.S. Pat. No. 9,050,161, which claims the benefit of U.S. Ser. No. 61/483,479, filed May 6, 2011, and U.S. Ser. No. 61/480,685, filed Apr. 29, 2011.

BACKGROUND

Currently, piezo style replaceable tips are not compatible with magnetostrictive ultrasonic medical and dental equipment, e.g., scalers. Separate operating systems are used for the two different types of devices, each with its own generator or power supply, handpieces, inserts, etc. which are specific to the particular device not interchangeable or useful with other devices or types of devices. Sometimes, for example, it is desired to use lights with or integrated into the equipment, to provide illumination to the work area for the primary device, and various attempts have been made to transfer power or light from or through the handpiece to the light emitting device.

There is a need in general for improvements in ultrasonic medical and dental equipment, and specifically for more versatility, interchangeability and adaptability of ultrasonic medical and dental equipment.

SUMMARY OF THE INVENTION

Disclosed herein is an insert receivable in an ultrasonic handpiece comprising a primary coil disposed about a well and electrically connected to a primary current supply, the insert comprising a secondary coil disposed about at least a portion of the insert dimensioned and arranged to be disposable within the well such that the secondary coil is inductively coupled to the primary coil, the secondary coil in electrical communication with at least one electrical device powered by the secondary coil. Accordingly, the energy to power an electrical device disposed on, in, or coupled to the insert is provided by induction of the power supplied by the handpiece power supply, which results in an amount of available energy previously unknown in such devices without requiring a direct electrical connection between an external power source and the electrical device. In an embodiment, a proximal portion of the insert carrying the secondary coil is disposable in the well and connected via a cable to a distal portion of the insert carrying the electrical device powered by the secondary coil.

In an embodiment, a tip-based computer-controlled tool system comprises an ultrasonic handpiece comprising a primary coil disposed about a well and electrically connected to a primary current supply; an insert comprising a secondary coil disposed about at least a portion of the insert dimensioned and arranged to be disposable within the well such that the secondary coil is inductively coupled to the primary coil, the secondary coil in electrical communication with at least one electrical device powered by the secondary coil; the electrical device comprising an operating characteristic controller enabled to control a value of an operating characteristic of at least one other electrical device, and a microprocessor coupled to the operating characteristic controller, the microprocessor comprising an algorithm for determining a desired value of an operating characteristic for the at least one other electrical device and adjusting the operating characteristic delivered to the at least one other electrical device to the desired value via the operating characteristic controller, the operating characteristic comprising a tip device profile corresponding to a tool attached to the insert, a proximity to one or more operating boundary parameters, a power level, a dental site temperature, a tool temperature, a dental hygiene material, a fluid type contained in a fluid supply, a safety feedback loop, an error circumstance, a pressure, a strain, or a combination thereof.

In an embodiment, a method of operating an ultrasonic handpiece comprising a primary coil disposed about a well and electrically connected to a primary current supply comprises disposing an insert into the well of the ultrasonic handpiece, the insert comprising a secondary coil disposed about at least a portion of the insert dimensioned and arranged to be disposable within the well such that the secondary coil is inductively coupled to the primary coil, the secondary coil being in electrical communication with at least one electrical device; supplying power to the primary coil via the primary current supply; and powering the at least one electrical device with the secondary coil via induction of the power from the primary coil into the secondary coil. In an embodiment, a proximal portion of the insert carrying the secondary coil is disposed in the well and connected via a cable to a distal portion of the insert carrying the electrical device powered by the secondary coil In an embodiment, a method of retrofitting a magnetostrictive ultrasonic handpiece comprising a primary coil disposed about a well and electrically connected to a magnetostrictive primary current supply comprises inserting an insert into the well of the ultrasonic handpiece, the insert comprising: a secondary coil disposed about at least a portion of the insert dimensioned and arranged to be disposable within the well such that the secondary coil is inductively coupled to the primary coil, the secondary coil in electrical communication with at least one electrical device powered by the secondary coil. In an embodiment, a proximal portion of the insert carrying the secondary coil is disposed in the well and connected via a cable to a distal portion of the insert carrying the electrical device powered by the secondary coil The instant disclosure expands the functionality of a magnetostrictive generator and in one embodiment makes it compatible with piezo style tips. In an embodiment, the instant disclosure discloses conversion of a magnetostrictive generator into a piezo ultrasonic generator. Such an instrument may be especially advantageous where a clinician may need to use a portable unit, e.g., in moving from one location to another.

In other embodiments, an insert for a handpiece is provided which harvests energy by induction like a transformer to power a variety of handheld instruments, especially dental and medical tools, such as, for example, caries and/or cancer detectors, high speed rotary machines, low speed rotary machines, curing lights, localized prophylactic and medicament dispensers, piezo scalers, and the like.

In an embodiment, electrical power to an electrical device, which may comprise a lighted element, is provided by utilizing the magnetic field flux generated in the handpiece of a magnetostrictive scaler. The magnetostrictive stack material is not only used to vibrate a connecting body and thusly a tip of a scalar, but is also utilized as a core in a coil or a plurality of coils of wire arranged as a secondary coil such that the secondary coil is inductively coupled to the primary coil, similar to the arrangement in a transformer, to generate electricity supplied to power at least one electrical device, which may include a light element.

BRIEF DESCRIPTION OF THE DRAWINGS

FIG. 5 is a perspective view of an insert according to an embodiment of the instant disclosure.

FIG. 6 is a cross sectional view of the assembly of FIG. 5 as seen along the lines 6-6.

FIG. 8 is a perspective view of a piezo insert assembled in a magnetostrictive handpiece according to another embodiment.

FIG. 9 is a cross sectional view of the assembly of FIG. 8 as seen along the lines 9-9.

DETAILED DESCRIPTION

Figure 1:
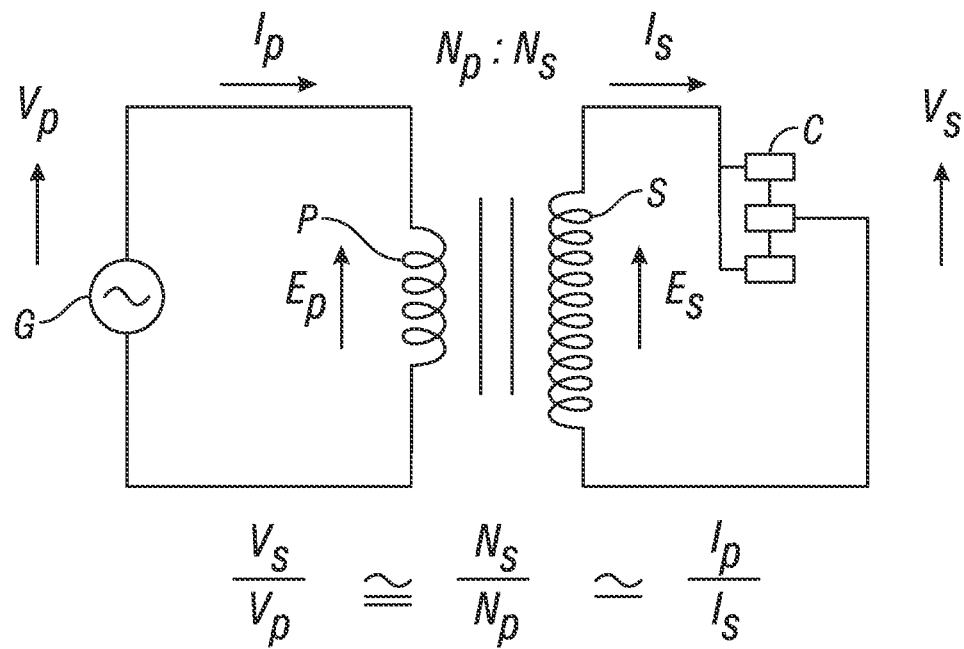
FIG. 1 is an electrical diagram for the insert assembly according to an embodiment of the instant disclosure.

At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the article or composition used/ disclosed herein can also comprise some components other than those cited. In the summary and this detailed description, each numerical value should be read once as modified by the term "about" (unless already expressly so modified), and then read again as not so modified unless otherwise indicated in context. Also, in the summary and this detailed description, it should be understood that a physical range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

As used in the specification and claims, "near" and "proximate to" is inclusive of "at."

The following definitions are provided in order to aid those skilled in the art in understanding the detailed description.

A magnetostrictive stack refers to an ultrasonic transducer, which typically comprise a plurality of elongated strips of magnetostrictive material, each strip having a proximal end and a distal end and are attached to its adjacent strip at the ends to form an integral substantially rigid column having a central axis with fins extending radially relative to said axis; and an ultrasonic resonant vibrator including such a transducer.

A piezoelectric stack refers to a plurality of piezo crystals arranged with a middle crystal as a first electrode and the end crystals as a second electrode. Energizing of the crystals results in vibrations travel through a piezo horn attached to the piezo crystals to the point or tip of a piezo scaler or other dental device. In the following description, a piezo scaler is referred to for exemplary purposes and is not intended as a limitation unless indicated to the contrary.

For purposes herein an ultrasonic handpiece comprising a primary coil disposed about a well and electrically connected to a primary current supply is also referred to herein as an ultrasonic handpiece, or simply as a handpiece. Likewise, a power supply to the handpiece refers to an external unit electrically connected to the handpiece which supplies the required power to the handpiece to operate the device consistent with its intended use. In addition, a power supply may further include the necessary hardware, connections, and controls to provide one or more fluids to the handpiece. Typical fluids include water or various aqueous solutions, compressed air or other gases, and the like.

For purposes herein an electrical device includes any device which requires electricity to operate consistent with its intended function. As used herein a detector refers to a device which senses or detects the intended parameter and which is able to evaluate and communicate this information to another entity separate from the detector. Accordingly, a temperature detector according to the instant disclosure refers to a device capable of determining the intended temperature and communicating the temperature via electronic communication to an external source, an internal controller, or the like. Direct electrical connection between the secondary coil and the electrical device indicates a direct wired link between the two.

As used herein, the terms primary coil and secondary coil are used consistent with their common use in the art wherein a primary coil refers to an electrical coil having power supplied to it by an external power supply. Likewise, a secondary coil refers to an electrical coil which is not in direct electrical contact with an external power supply, but instead receives power through induction by being inductively coupled with a primary coil.

As used herein, the turn ratio of the secondary coil relative to the primary coil is defined as the number of turns of the secondary coil divided by the number of turns on the primary. A turn ratio of greater than one increases the voltage induced by the secondary coil relative to the primary coil and a turn ratio of less than one decreases the voltage induced by the secondary coil relative to the primary coil.

For purposes herein, relative magnetic permeability, which is also referred to as relative permeability, and which may also be referred to simply as permeability is a variation upon 'straight' or absolute permeability, g. Relative magnetic permeability is a measure of how the presence of a particular material affects the relationship between flux density and field strength. Relative magnetic permeability is defined in relation to the permeability of a vacuum, go, according to the following equation:

$$\mu_r = \mu/\mu_0 \qquad \text{Equation MPE}$$

wherein to $\mu_0 = 4\pi \times 10^{-7}$ V·s/(A·m)$\approx 1.2566370614\ldots \times 10^{-6}$ H·m$^{-1}$ or N·A$^{-2}$ or T·m/A or Wb/(A·m).

For example, if you use a material for which $\mu_r = 3$ then you know that the flux density will be three times as great as it would be if we just applied the same field strength to a vacuum. $\mu_r$ is a dimensionless ratio having no units associated with it.

As used herein a magnetostrictively inactive core refers to a material which is typically not utilized for producing magnetostrictive movement. While it to be understood that essentially any material may exhibit magnetostrictive oscillation if positioned in a strong-enough oscillating magnetic field, a magnetostrictively inactive metallic core is defined as a material having a magnetostrictive coefficient, L, at saturation which is less than or equal to that of iron under the same conditions. For example, the saturation magnetostrictive coefficient of iron is reported to be about $1.1$-$2.0*10^{-5}$ (see Brown, W. F., Magnetic Materials, Ch 8 in the Handbook of Chemistry and Physics, Condon and Odishaw, eds., McGraw-Hill, 1958). Accordingly, a magnetostrictively inactive core may have a magnetostrictive coefficient at saturation of less than $2.0*10^{-5}$.

The term magnetostrictive materials refer to those materials understood by one of skill in the art to be useful for converting magnetic energy into kinetic energy, or the reverse, as demonstrated by their use in building actuators and sensors. The property can be quantified by the magnetostrictive coefficient, L, which is the fractional change in length as the magnetization of the material increases from zero to the saturation value. The effect is responsible for the familiar "electric hum" which can be heard near transformers and high power electrical devices.

Examples of magnetostrictive materials for purposes herein include those having similar properties compared to cobalt, which exhibits the largest room temperature magnetostriction of a pure element at 60 microstrains. Other examples include alloys, including Terfenol-D, Tb$_x$Dy$_{1-x}$Fe$_2$, and the like which exhibit about 2,000 microstrains in a field of 2 kOe (160 kA/m) at room temperature. Another very common magnetostrictive composite is the amorphous alloy Fe$_{81}$Si$_{3.5}$B$_{13.5}$C2 with its trade name Metglas 2605SC, and the like which has a high saturation magnetostriction constant, $\lambda$, of about 20 microstrains or more, coupled with a low magnetic anisotropy field strength, HA, of less than 1 kA/m (to reach magnetic saturation).

In an embodiment, an insert receivable in an ultrasonic handpiece comprising a primary coil disposed about a well and electrically connected to a primary current supply comprises a secondary coil disposed about at least a portion of the insert dimensioned and arranged to be disposable within the well such that the secondary coil is inductively coupled to the primary coil, the secondary coil in electrical communication with at least one electrical device powered by the secondary coil.

In an embodiment, the ultrasonic handpiece acts as a source of power for the electrical devices present on, imbedded in, or associated with the insert and/or the handpiece. In an embodiment, the electrical devices may comprise piezo actuators embedded in, disposed on, attached to, or otherwise associated with an insert.

Turning to FIG. 1, the handpiece generally comprises a primary coil P disposed about a well in which the magnetostrictive insert is normally received. In an embodiment the insert need not comprise a magnetostrictive stack, but may comprises a rod or other suitably shaped object which functions as a core element to the secondary coil receivable within the well of the handpiece made of stainless steel or another core material having a relative magnetic permeability greater than one. In an embodiment, the insert may comprise a magnetostrictive stack, which also functions as the core element to the secondary coil.

A secondary coil S is wound about the core with a number of turns about one or more axes. The alternating current Ip and voltage Vp supplied from the magnetogenerator G passing through the primary coil P in the handpiece induces a current in the secondary coil S to apply a secondary voltage Vs and secondary current Is to the one or more electrical devices C of the insert. Accordingly, the secondary coil of the insert in proximity to the primary coil of the handpiece and inductively coupled to the primary coil and thus functions as a transformer to convert the primary coil electrical potential Ep to the secondary coil electrical potential Es, as is readily understood by one of minimal skill in the art. In an embodiment, no movement of the insert is required to produce power for the one or more electrical devices of the insert, the handpiece, or both. Even when the insert includes a magnetostrictive stack and thus undergoes oscillation when power is supplied to the primary coil of the handpiece, the mechanical energy produced by the oscillation provided to the insert by the magnetostrictive stack is not converted into electrical energy. In an embodiment, all of the power supplied to the one or more electrical devices is provided by induction of energy present in the primary coil into the secondary coil disposed on the insert.

For example, the voltage induced across the secondary coil can be estimated from Faraday's law of induction and the turns ratio, Ns/Np, where Ns is the number of turns of the secondary coil (on the insert) and Np is the number of turns of the primary coil (in the handpiece). Since inductively coupled coils have a relatively high efficiency, the ideal transformer equations, Vs/Vp=Ns/Np=Ip/Is, are a reasonable approximation, i.e., Vs/Vp≈Ns/Np≈Ip/Is, as shown in FIG. 1.

Piezoelectric oscillators used in dental scalers typically have a series of quartz or other crystals with resonant frequency around 25 to 30 kHz, which is coincidentally similar to that of magnetostrictive devices. However, piezoelectric oscillators typically operate at a much higher voltage than required by a magnetostrictive ultrasonic transducer. The piezo insert for a particular handpiece/generator unit may be designed with a matching resonant frequency. The turn ratio of the secondary coil relative to the primary coil will normally be greater than 1 in one embodiment, greater than 5 or greater than 10 in other embodiments, as is required to step up the voltage from the normal operating range of the magnetostrictive handpiece to that required to operate the piezo unit or another electrical device. Likewise, in an embodiment, the turn ratio of the secondary coil relative to the primary coil may be less than 1 in one embodiment, less than 0.5 or less than 0.10 in other embodiments, as is required to step down or lower the voltage from the normal operating range of the magnetostrictive handpiece to that required to operate the particular electrical device.

Figure 2:
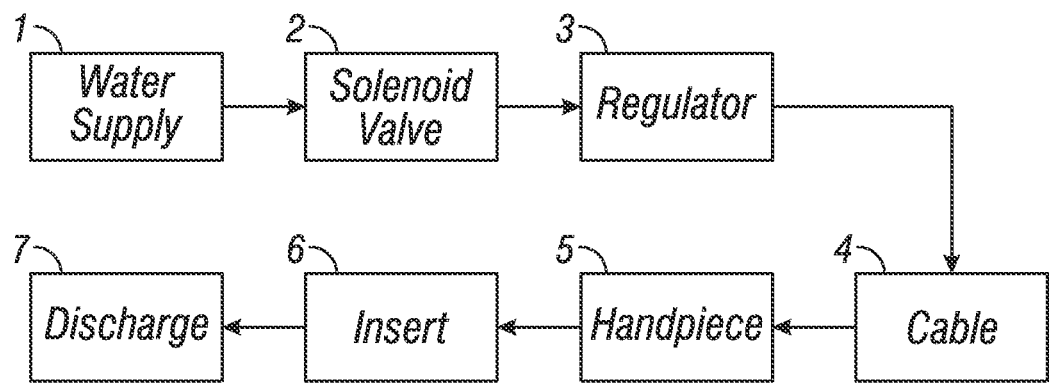
FIG. 2 is a block flow diagram for the water supply to the handpiece/insert assembly according to an embodiment of the instant disclosure.

In an embodiment, the power supply module of the handpiece also supplies water and/or compressed air to the handpiece which provides cooling and facilitates debris removal from the dental working surfaces being cleaned. As shown in FIG. 2, the water flow diagram for a piezo and magneto scaler handpiece is similar, passing from the water supply 1, through a solenoid valve 2 and regulator 3 which may if desired be disposed in the power supply unit. From the regulator 3, the water flows through a tube in the cable 4 to the handpiece 5 to provide cooling to the piezo or other insert 6 and finally flows out of the insert through a discharge port 7, which may be located to clean and/or cool the working surface or area. In one embodiment the cable 4 supplying the water is the same cable supplying electrical power to the handpiece 5 via electrically insulated wires.

The ultrasonic handpiece suitable for use herein are readily available and known in the art. In one embodiment, the handpiece is based on a power generating unit and handpiece available from Ultrasonic Services, Inc. under the trade designation USI 25MPLC (Ultrasonic Services, Inc., Houston, Tex.) using power level control technology, or one of the power generators as disclosed in U.S. Pat. No. 6,164,968; U.S. Pat. No. 6,503,081; U.S. Pat. No. 6,893,261; U.S. Pat. No. 6,976,843; U.S. Pat. No. 7,150,629; or the like, each of which incorporated herein by reference in its entirety.

Figure 3:
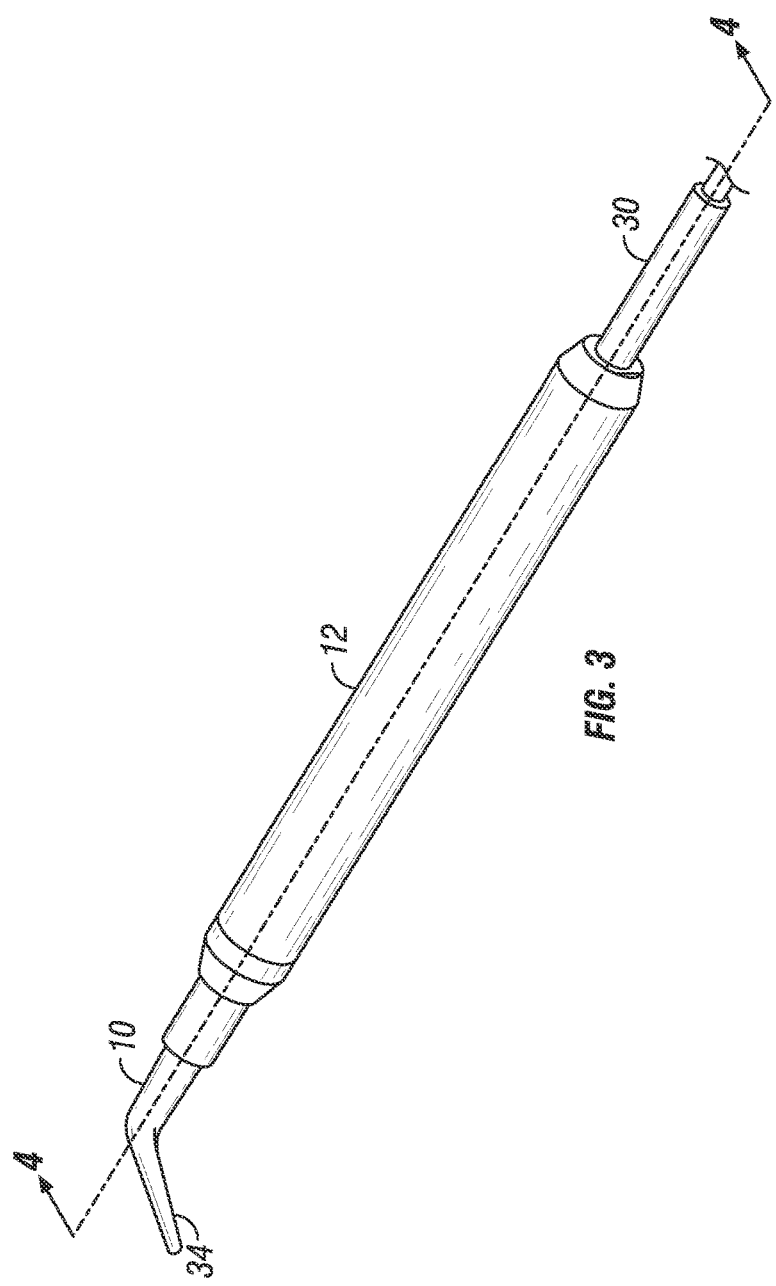
FIG. 3 is a perspective view of a piezo insert assembled in a magnetostrictive handpiece according to an embodiment of the instant disclosure.
Figure 4:
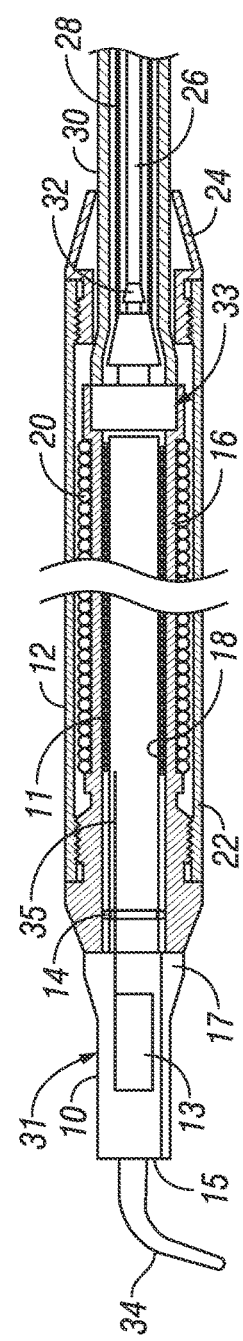
FIG. 4 is a cross sectional view of the assembly of FIG. 3 as seen along the lines 4-4.

As seen in FIGS. 3 and 4, the insert 10 is placed inside a suitable handpiece 12 by frictional engagement, for example, by means of O-ring 14, and supplied with power to the primary coil 20. The handpiece 12 in one embodiment comprises an inner cylindrical 16, with an inside diameter forming the well 18 and around which the wire is wrapped to form the primary coil 20, and an outer cylindrical piece 22 threaded to the inner cylindrical piece 16 at one end and threaded to engage tail nut 24 at the other end.

The water tubing 26 and primary power supply wires 28 are protected in a cable sheath 30 which is in fluid and electrical connection with a conventional power/water supply unit (not shown). Commercially available power supply units include the USI 25 PLC, USI 30 PLC (Ultrasonic Services, Inc., Houston, Tex.) and/or the like. In an embodiment, water or another fluid is supplied to the handpiece 12 via the tubing 26 and nipple fitting 32 and flows through well 18 receiving the insert 10 to provide cooling to the secondary coil 11 disposed about at least a portion of insert 10 dimensioned and arranged to be disposable within well 18 such that secondary coil 11 is inductively coupled to primary coil 20. Secondary coil 11 is in electrical communication with at least one electrical device 13 powered by secondary coil 11.

As is shown in FIG. 4, after the water contacts at least a portion of insert 10 proximate to secondary coil 11, the water may exit the handpiece, conventionally adjacent the tip 34 through flow passages 15 formed in insert 10. Accordingly, in an embodiment wherein the ultrasonic handpiece further comprises a water supply in fluid connection with the well, and wherein water supplied to the ultrasonic handpiece contacts at least a portion of the insert proximate to the secondary coil prior to the water exiting the ultrasonic handpiece.

Secondary coil 11 is excited or energized by passing an alternating current supplied via wires 28 through primary coil 20 formed in the shell of handpiece 12. A voltage and electrical current is produced in secondary coil 11 via induction from primary coil 20. The voltage from secondary coil 11 causes the one or more electrical devices 13 (e.g., a piezo crystal stack) to oscillate, and the vibration is transmitted conventionally through the piezo horn 17 and then to tip 34.

In an embodiment, a handheld electrical tool system comprises a handpiece comprising a primary coil disposed about a well and electrically connected to a primary current supply (see FIG. 2); an insert 10 comprising a distal portion 31 and a proximal portion 33. In an embodiment, the proximal portion 33 being magnetostrictively inactive. In an alternative embodiment, the proximal portion may be magnetostrictive. In an embodiment, the proximal portion 33 is dimensioned and arranged to be removably disposed within the well 18. The handheld electrical tool system further including an electrical device 13 located on the insert 10; a secondary coil 11 disposed about and in contact with the proximal portion 33 of the insert 10 to inductively couple to the primary coil 20 when the proximal portion 33 of the insert 10 is disposed within the well 18 to provide a secondary current supply; and a circuit 35 to electrically connect the electrical device 13 to the secondary current supply.

In an embodiment, the electrical device powered by the secondary coil may comprise one or more of a piezoelectric crystal stack, caries detectors, cancer detectors, temperature detectors, density detectors, strain detectors, conductivity detectors, power level detectors, high speed rotary machines, low speed rotary machines, spectroscopic detectors, prophylactic dispensers, medicament dispensers, imaging devices, operational controllers, microprocessors, memory modules, communication devices, an electromagnet, an ac to dc converter or a combination thereof. In an embodiment, wherein the electrical device comprises an electromagnet, the electromagnet may further include an ac/dc converter and associated control circuitry to produce a direct current from the alternating current produced by the secondary coil. Accordingly, in an embodiment, the electromagnet may be a constant state electromagnet. In an embodiment, the electromagnet may be a variable field electromagnet suitable to produce varying magnetic flux.

In an embodiment, the electrical device may include an electromagnet suitable for use as a magnetic pickup tool. In an embodiment, the electrical device may include an electromagnet suitable for use in producing a cure in magnetically cured composites.

In an embodiment, the electrical device powered by the secondary coil may comprise illumination lights, curing lights, or a combination thereof, wherein the insert comprises a magnetostrictively inactive core.

In an embodiment, the electrical device may comprise a component of an operating characteristic control system enabled to control a value of an operating characteristic of at least one other electrical device. Operating characteristic controllers are disclosed, for example, in U.S. Patent publication US 2010/0036535, which is hereby fully incorporated herein by reference in its entirety. In an embodiment, the electrical device may comprise a microprocessor coupled to the operating characteristic control system, the microprocessor comprising an algorithm for determining a desired value of an operating characteristic for the at least one other electrical device and adjusting the operating characteristic delivered to the at least one other electrical device to the desired value via the operating characteristic controller. In an embodiment, the operating characteristic comprises a tip device profile corresponding to a tool attached to the insert, a proximity to one or more operating boundary parameters, a power level, a dental site temperature, a tool temperature, a dental hygiene material, a fluid type contained in a fluid supply, a safety feedback loop, an error circumstance, a pressure, a strain, or a combination thereof.

Figure 7:
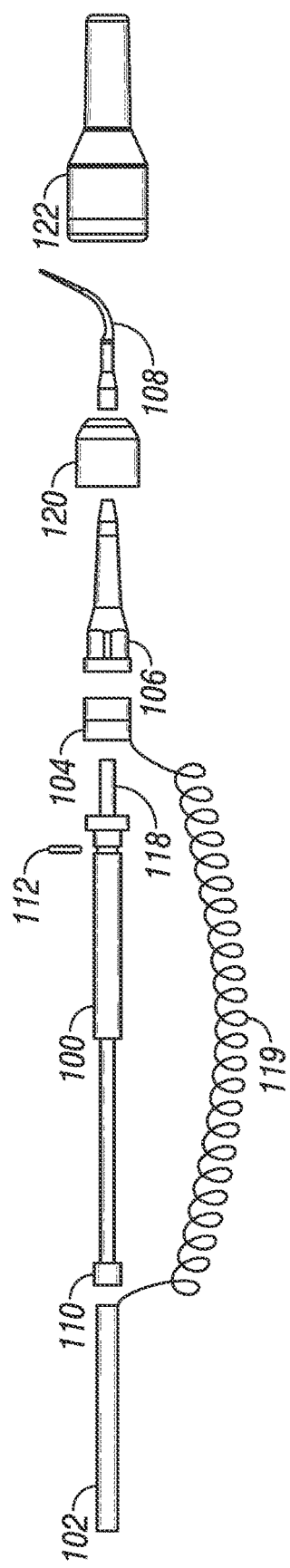
FIG. 7 is an exploded view of the insert of FIGS. 5-6.

An example of an insert 10A is shown in FIGS. 5, 6 and 7. In this embodiment, the electrical device comprises a piezo insert, and thus may be used in retrofitting a magnetostrictive ultrasonic handpiece comprising a primary coil disposed about a well and electrically connected to a magnetostrictive primary current supply by inserting a piezo insert according to an embodiment of the instant disclosure into the handpiece.

In an embodiment, insert 10A comprises a secondary coil 102 disposed around at least a portion of a magnetostrictively inactive metallic core 100 having a relative magnetic permeability of greater than 1, or greater than 5, or greater than 100, or greater than 1000, or greater than 10,000. In an embodiment, the metallic core 100 may comprise stainless steel. In an embodiment, core 100 is wound with a secondary coil 102 to supply a secondary current to one or more electrical devices, e.g., a piezo crystal stack 104, which transmits vibration through the horn 106 to the tip 108 connected thereto, e.g., by threading. Accordingly, in an embodiment, the electrical device comprises a piezoelectric stack mechanically coupled to a horn, the horn coupled to or couple-able to a tip, wherein a tip if couple-able if it can be removed and then reattached.

Accordingly, in an embodiment, the handheld electrical tool system may further comprise an insert inventory comprising a plurality of the inserts 108 for the handpiece 100, wherein the inserts are interchangeable in the handpiece and the electrical devices of the respective ones of the plurality of inserts are the same or different.

Likewise, in an embodiment, the handheld electrical tool system may further comprise an insert inventory comprising a plurality of interchangeable inserts for the handpiece, wherein the inventory comprises at least the electrical device insert and an ultrasonic magnetostrictive insert, and a magnetostrictive power generator to provide the primary current with characteristics to selectively operate the ultrasonic magnetostrictive insert and the electrical device insert.

In an embodiment, core 100 includes an enlarged distal end 110 which is dimensioned and arranged to retain secondary coil 102 and may further provide a back mass for the piezo crystal stack 104.

In an embodiment, a proximal end of core 100 supports an o-ring 112 for frictional engagement in the handpiece as described above, and a washer 114 to retain the piezo crystal stack 104. The washer 114 is shouldered around a proximal extension 118 of core 100 which extends into a bore in the annular-shaped piezo crystal stack 104 to provide engagement of the piezo stack to horn 106, e.g., by threading. A non-conductive (e.g., plastic) case 120 may be provided for piezo stack 104, and/or for other electrical devices to provide isolation of the electrical device from water or an external environment. An overall or outer housing 122 may also be provided for proximal end of the insert 10A.

In an embodiment, core 100 may include a lateral bore or conduit 113 arranged behind O-ring 112 in communication with a central proximal bore 115 to supply cooling water from the handpiece well, through or around the electrical device (e.g., crystal stack 104) in fluid communication with an external environment through one or more outlets 117 located at or near tip 108. In an embodiment, secondary coil 102 comprises wires insulated with a thin resin coating with similarly insulated leads 119 to provide direct electrical communication with the one or more electrical devices, e.g., piezo crystal stack 104.

In an embodiment, the insert 10A is adapted to be powered and used in a conventional magnetostrictive handpiece with a magnetostrictive power supply. Thus the magnetostrictive handpiece and the associated power supply unit can be converted to a piezo type unit with an insert comprising a piezo stack, with no other changes to the magnetostrictive handpiece or power supply unit required, other than changing the insert according to an embodiment of the instant disclosure. In an embodiment, tuning of the power supply unit may be required for operation. The magnetostrictive power supply can employ manual tuning or automatic tuning with a feedback circuit as is known in the art to detect resonant frequency based on power consumption, with or without offset tuning.

A magnetostrictive ultrasonic power scaler can thus be adapted or retrofit to power a piezo insert, based on microprocessor technology in one embodiment, and provide advanced features such as comfort and ease of a manual tuned unit, utilization of any operating frequency, automatic water control, RFID technology, or any combination thereof. For example the unit can use one or more features from U.S. Pat. No. 6,503,081 U.S. Pat. No. 6,893,261; U.S. Pat. No. 6,976,843; U.S. Pat. No. 7,150,629; or the like, each of which incorporated herein by reference in its entirety.

Figure 10:
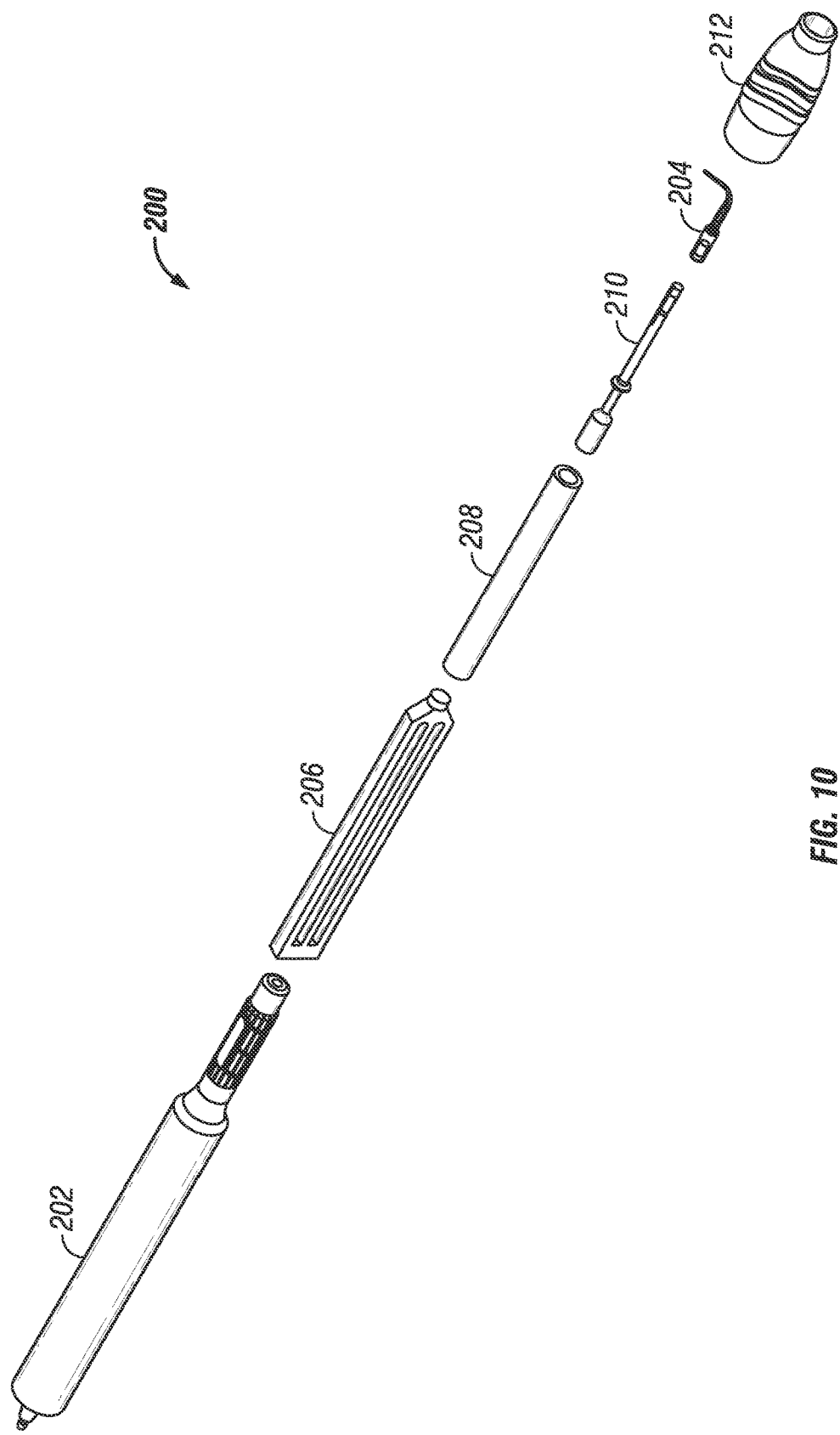
FIG. 10 is a partially exploded view of the insert of FIGS. 8-9.

In an embodiment as shown in FIGS. 8-10, the insert 200 may comprise a conventional or specially adapted insert having a portion 202 dimensioned and arranged to be disposable within a well of a handpiece such that the secondary coil 208 is inductively coupled to the primary coil of the handpiece. The secondary coil 208 is wrapped around or otherwise disposed around at least a portion of a magnetostrictively inactive metallic core 206 having a relative magnetic permeability of greater than 1. Core 206 is attached to horn/connector body 210 comprising one or more electrical devices 211 in electrical communication with secondary coil 208, and a grip member 212. Horn 210 is coupled or couple-able to tip 204. In an embodiment, insert 200 is constructed in the same general manner as the assembly of FIGS. 3-7, except core 206 comprises a high magnetic permeability material having a relative magnetic permeability of greater than 1, or greater than 5, or greater than 10, or greater than 100, or greater than 1,000, or greater than 10,000 and comprises at least three longitudinal sections 213 and 214 spaced laterally apart and joined via transverse members 215 and 216 at either end. Secondary coil 208 is wound around central longitudinal section 214, passing through the spaces between the outer longitudinal members 213. Such an arrangement improves the efficiency of the induction of the power from a primary coil. In an embodiment, secondary coil 208 may be encased in a non-conductive polymer matrix, e.g., epoxy. In an embodiment, a plurality of secondary coils may be similarly arranged in the insert collinear with the secondary coil, or sequentially arranged along a central axis of the core (not shown) depending on the power needs for the one or more electrical devices powered by the secondary coils.

Figure 11:
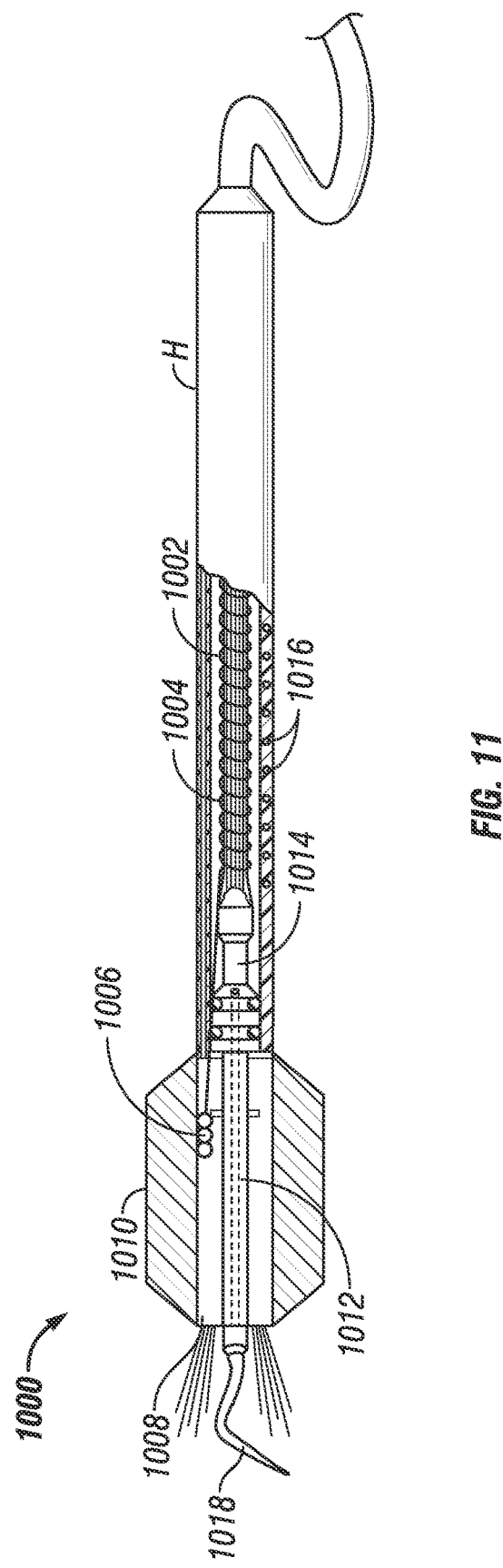
FIG. 11 is a partial cross-sectional perspective view of a handpiece, dental scaling insert, secondary circuit and lighting element according to an embodiment.

As shown in FIG. 11, in an embodiment an insert 1000 according to the instant disclosure may comprise one or more secondary coil(s) 1002 disposed about a core comprising a magnetostrictive stack 1004, wherein secondary coil 1002 is in electrical connection with one or more electrical devices, which may include one or more light-emitting diode (LED) assemblies 1006 or another light producing element, which in an embodiment may be further optically associated with light guide 1008 which may be annular and disposed between an outer grip 1010, which may be opaque, and a centrally disposed shank 1012 of a velocity transducer 1014.

The insert 1000 in one embodiment thus provides for vibration of the tip 1018 or other tool as well as power for the lighting element 1006 to light the work area as required by the operator.

In operation, insert 1000 is placed in the handpiece H and operated as a scaler in the normal fashion wherein ultrasonic oscillation is provided by magnetostrictive stack 1004. The handpiece H provides magnetic induction via primary coil 1016 in the wall of the handpiece. The magnetostrictive stack 1004 is oscillated by the magnetic flux in the usual manner, except that a relatively minor portion of the flux produced by primary coil 1016 is induced as an electrical current in the secondary coil(s) 1002, which powers the LED assembly 1006, and any other electrical device present. Light from the LED assembly 1006 passes through the light guide 1008 to illuminate a work area near the tip 1018 or other tool. It is to be understood that in an embodiment according to the instant disclosure, when the insert includes a magnetostrictive stack and thus undergoes oscillation when power is supplied to the primary coil of the handpiece, the mechanical energy produced by the oscillation provided to the insert by the magnetostrictive stack is not converted into electrical energy. In an embodiment, all of the power supplied to the one or more electrical devices associated with the insert is provided by induction of energy present in the primary coil into the secondary coil disposed on the insert.

Figure 12:
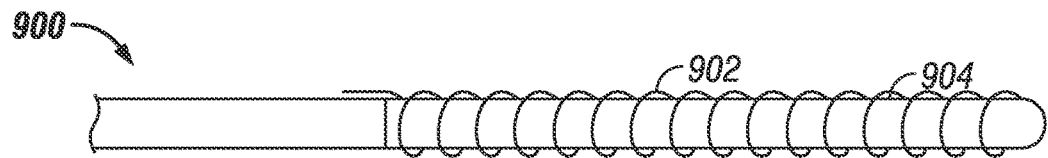
FIG. 12 is a schematic diagram of a portion of a magnetostrictive stack and full-length secondary coil according to an alternate embodiment of FIG. 11.
Figure 13:
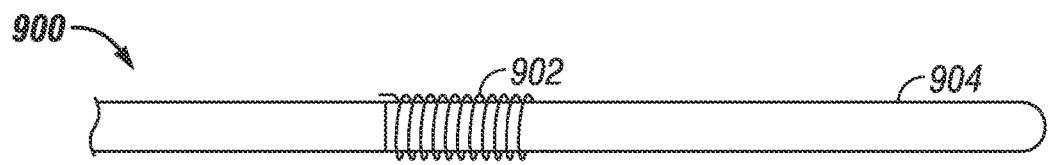
FIG. 13 is a schematic diagram of a portion of a magnetostrictive stack and partial-length secondary coil according to an alternate embodiment of FIG. 11.

In an embodiment, insert 900 may comprise secondary coil(s) 902 disposed along substantially all (see FIG. 12) or a portion (see FIG. 13) of core 904. Core 904 may include a standard profile (i.e., having the same diameter along the length of the core) with secondary coil(s) 902 wound thereon or provided in the form of a sleeve which is fitted over core 904, where the insert is to be employed in a handpiece H with adequate clearance to accommodate the increased transverse dimensions from addition of the secondary coil(s).

Figure 14A:
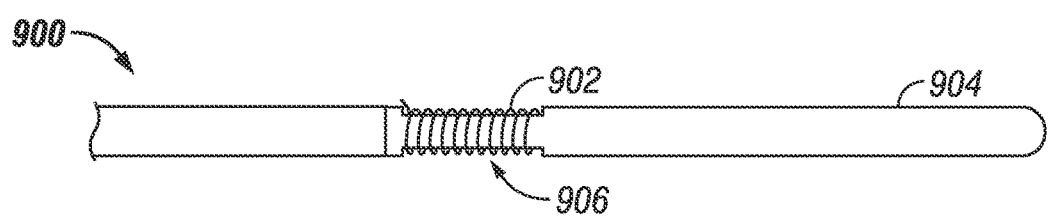
FIG. 14A is a schematic diagram of a portion of a magnetostrictive stack and a profiled secondary coil according to an alternate embodiment of FIG. 11.
Figure 14B:
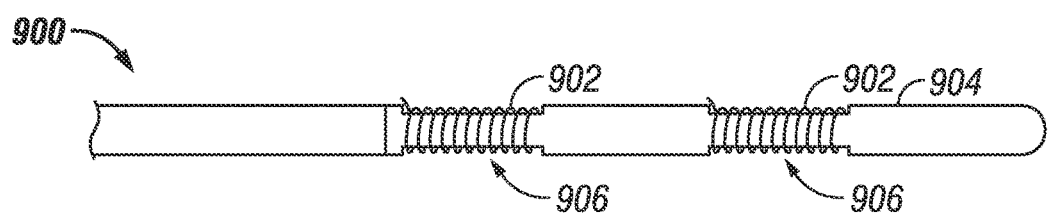
FIG. 14B is a schematic diagram of a portion of a magnetostrictive stack and a plurality of profiled secondary coils according to an alternate embodiment of FIG. 11.

In another embodiment, the insert 900 may include a core 904 comprising a profile which has a recess 920 (see FIG. 14A) to receive the secondary coil(s) 902 so that the coil does not increase the transverse dimensions of the core 902, or increases the transverse dimensions only where the lead wires from the coil(s) 902 traverse the outer surface of the core 904 to provide electrical connection between the secondary coil 902 and the one or more electrical device (not shown) As shown in FIG. 14B, a plurality of coils 902 may be used, which may be the same of different, and may be disposed end to end along the core 904, or they can be nested or intertwined (not shown), or any desired combination. The use of a plurality of different secondary coils allows for providing different voltages and power requirements to various electrical devices. In addition, a plurality of coils 902 can be wired in parallel and/or in series.

Figure 15:
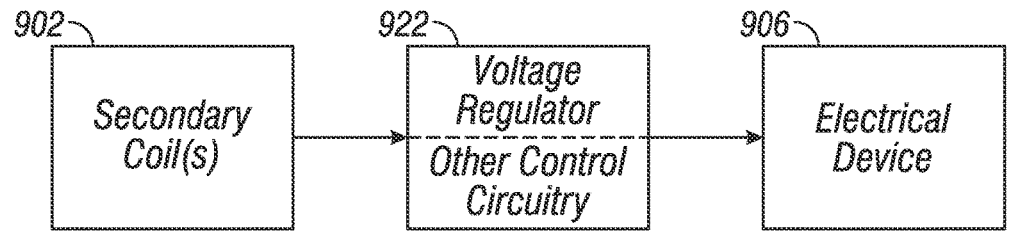
FIG. 15 is a schematic electrical diagram for an embodiment of the self-lighting magnetostrictive insert of FIG. 11.

As shown in FIG. 15, secondary coil(s) 902, the one or more electrical device, (e.g., LED assembly) 906 and the associated wires and components are constructed and arranged on or in the core to resist fatigue stresses due to the vibration of the insert 900. To avoid overpowering the one or more electrical device 906 and to maintain a constant level of power to the device regardless of any modulation of the power input to the primary coil 916, the insert may further comprise a voltage regulator or other control circuitry 922 as shown in the circuit diagram of FIG. 15.

Figure 16:
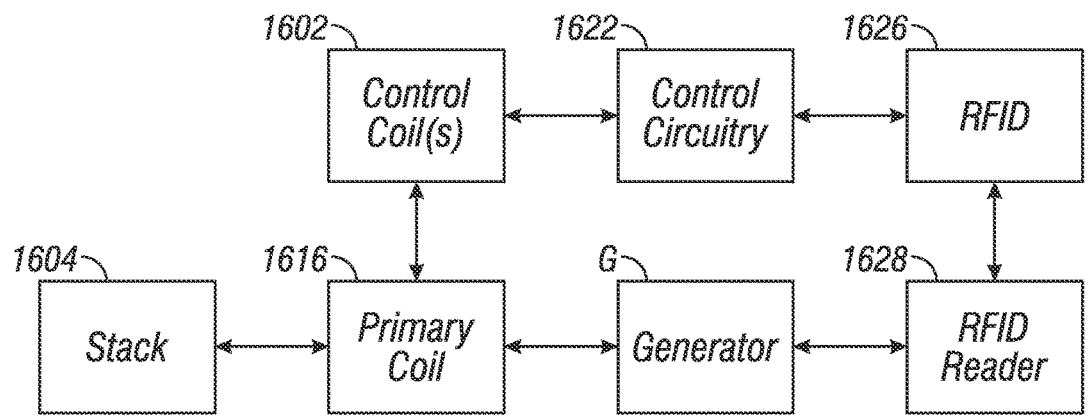
FIG. 16 is a control schema for a tool- or tip-controlled insert according to another embodiment.

With reference to FIG. 16, in an embodiment, the insert 900 may comprise a tool-control schema comprising circuitry configured to modify the energy available to the secondary coil to control power to the one or more electrical devices. When the insert comprises a magnetostrictive stack 1604, control circuitry 1622 embedded in the insert 900 (see FIGS. 12 to 14B) may be adapted to modify the vibration of the driven element associated with the magnetostrictive stack such as a tip, cutting tool, or the like, by dampening or enhancing the vibrations of the magnetostrictive stack 1604. In an embodiment, the magnetic energy available to magnetostrictive stack 1604 can be attenuated or intensified by using the one or more secondary coil(s) 1602 which function by adjusting the amount of power drawn from the secondary coil(s) 1602, e.g., by draining power from the handpiece primary coil 1616 and increasing or reducing the amount of power drained, and/or by using one or more of the secondary coils 1602 to produce dampening or reinforcing magnetic fields. In an embodiment wherein the insert does not comprise a magnetostrictive core element, one or more secondary coil(s) 1602 may be employed as an auxiliary or control coil coaxially aligned or otherwise positioned within the flux field of another secondary coil which supplies power to one or more electrical devices.

Placement of control circuitry 1622 and a secondary coil 1602 which functions as a control coil in the insert 900 (see FIGS. 12 to 14B) provides primary control of the tool within the tool and/or insert, allowing some or all of the conventional control functionality to be removed from the generating device. Some benefits of this schema would include faster response time to varying tool load conditions (e.g., when the calculus is removed or tissue is penetrated), control of tool operating or other characteristics by the tool itself rather than the generator (allowing a wider range of generators equipped or not with the appropriate conventional controls to be otherwise used for the tool), higher performance qualities which could reduce operator skill level requirements (e.g., where a skilled operator might use "feel" to operate the tool), faster learning curve for operators, enhanced patient comfort, and the like.

In an embodiment, the insert may comprise bidirectional communication circuitry powered by a secondary coil to provide electronic communication with the ultrasonic generator G, for example, via an RFID 1626 (FIG. 16) and reader 1628 as disclosed in U.S. Patent publication US 2010/0036535, incorporated by reference herein, such that the insert provides some or all of the control functions and cooperate with any generator control functionality to further enhance operation of the insert.

In an embodiment, a tip-based computer-controlled tool system comprises an ultrasonic handpiece comprising a primary coil disposed about a well and electrically connected to a primary current supply, an insert comprising a secondary coil disposed about at least a portion of the insert dimensioned and arranged to be disposable within the well such that the secondary coil is inductively coupled to the primary coil, the secondary coil in electrical communication with at least one electrical device powered by the secondary coil, the electrical device comprising an operating characteristic controller enabled to control a value of an operating characteristic of at least one other electrical device, and a microprocessor coupled to the operating characteristic controller, the microprocessor comprising an algorithm for determining a desired value of an operating characteristic for the at least one other electrical device and adjusting the operating characteristic delivered to the at least one other electrical device to the desired value via the operating characteristic controller, the operating characteristic comprising a tip device profile corresponding to a tool attached to the insert, a proximity to one or more operating boundary parameters, a power level, a dental site temperature, a tool temperature, a dental hygiene material, a fluid type contained in a fluid supply, a safety feedback loop, an error circumstance, a pressure, a strain, or a combination thereof.

Figure 17:
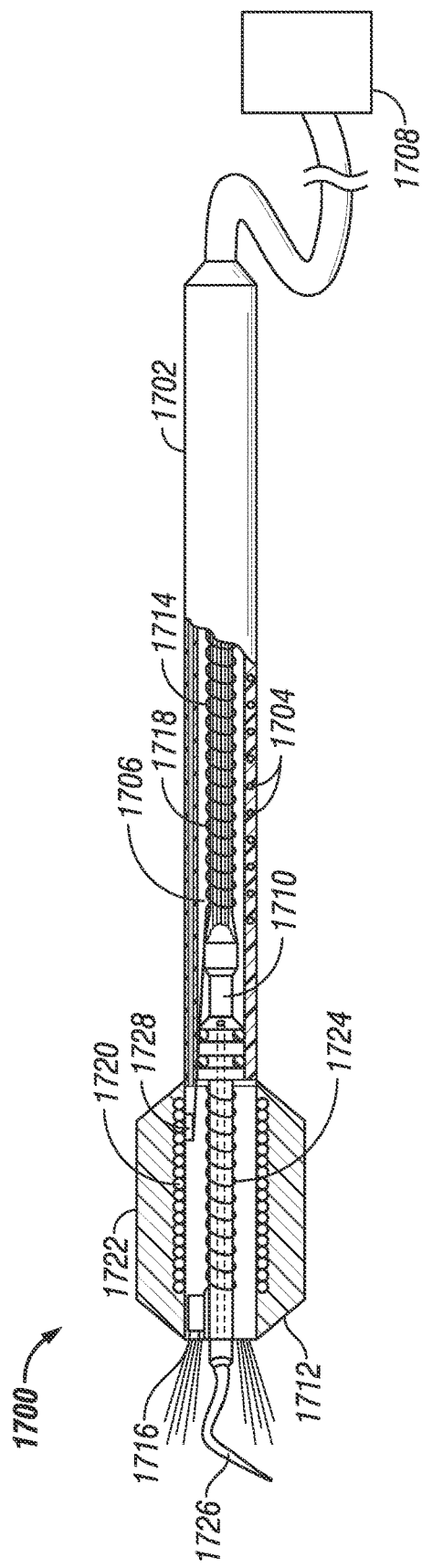
FIG. 17 is a partial cross-sectional perspective view of a handpiece, dental scaling insert, secondary circuit and tertiary circuit according to an embodiment.

As shown in FIG. 17, in an embodiment, the a handheld electrical tool system 1700 comprises a handpiece 1702 comprising a primary coil 1704 disposed about a well 1706 and electrically connected to a primary current supply 1708; an insert 1710 comprising a distal portion 1712 and a proximal portion 1714, the proximal portion 1714 dimensioned and arranged to be removably disposed within the well 1706; an electrical device 1716 located on the insert 1710, wherein the electrical device 1716. A secondary coil 1718 is disposed about and in contact with the proximal portion 1714 of the insert 1710 to inductively couple to the primary coil 1704 when the proximal portion 1714 of the insert 1710 is disposed within the well 1706 to provide a secondary current supply 1728 to a tertiary coil 1720 disposed within a grip 1722 of the insert 1710 located on the distal portion 1712 of the insert 1710; and a quaternary coil 1724 inductively coupled to the tertiary coil 1720; and a circuit 1726 to electrically connect the electrical device 1716 to the quaternary coil 1724.

In an embodiment, the handheld electrical tool system further comprises a tertiary coil disposed within a grip located on the distal portion electrically connected to the secondary coil; and a quaternary coil disposed about and in contact with the distal portion inductively coupled to the tertiary coil to provide a tertiary current supply, and a circuit to electrically connect the electrical device to the tertiary current supply.

In an embodiment, the electrical device 1716 is selected from the group consisting of a piezoelectric crystal stack, caries detector, cancer detector, temperature detector, density detector, strain detector, conductivity detector, power level detector, high speed rotary machine, low speed rotary machine, illumination light, curing light, spectroscopic detector, prophylactic dispenser, medicament dispenser, imaging device, operational controller, microprocessor, memory module, communication device, electromagnet, ac/dc converter, and combinations thereof.

Figure 18:
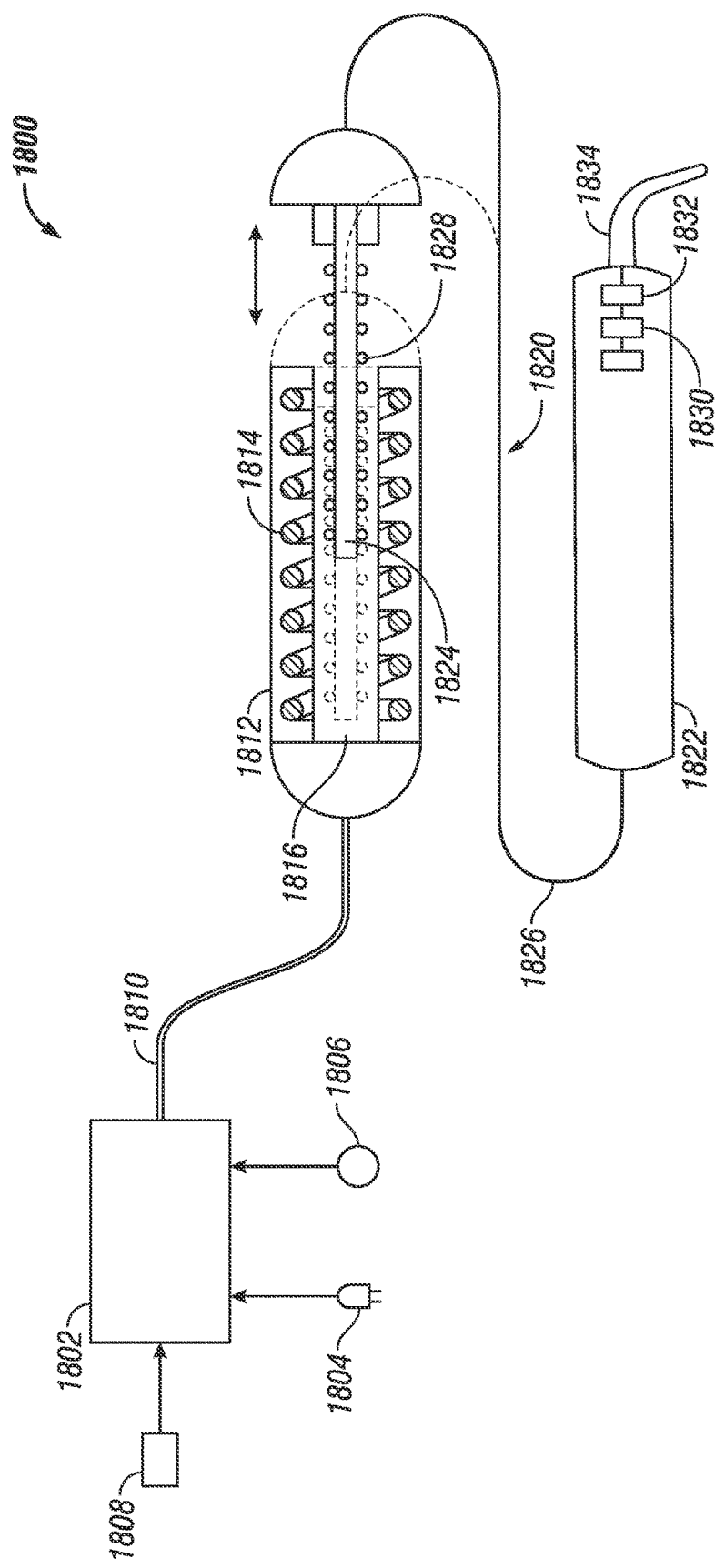
FIG. 18 is a schematic diagram of a system where a proximal portion of the insert carrying the secondary coil is connected via a cable to a distal portion of the insert carrying the electrical device powered by the secondary coil.

As shown in FIG. 18, in an embodiment, the system 1800 has a power generator unit 1802, which may be a conventional unit for a magnetostrictive dental scaler, e.g., connected to a power supply 1804, a fluid (e.g., water) supply 1806, and an optional footswitch 1808, which may be an on-off footswitch or a power level control footswitch as desired. The unit 1802 supplies water and/or a conditioned power supply via cable 1810 to handpiece 1812, which has primary coil 1814 disposed about well 1816 and is electrically connected to the current supply from the generator 1802 via the cable 1810. The unit 1802, power supply 1804, fluid supply 1806, cable 1810, and handpiece 1812, including primary coil 1814 and well 1816 may be conventional, e.g., adapted to receive a standard magnetostrictive insert, such as for example, an insert for dental scaling with an operating frequency of about 25 kHz, all as described in embodiments above.

The system 1800 also includes an insert 1820 comprising a distal portion 1822 and a proximal portion 1824 connected via cable 1826 such that the distal portion 1822 may be mechanically separated (as permitted by cable 1826) and/or disposed remotely from the proximal portion 1824. The proximal portion 1824 in this embodiment is likewise dimensioned and arranged to be removably disposed within the well 1816. A secondary coil 1828 is disposed about the proximal portion 1824 to inductively couple to the primary coil 1814, when the proximal portion 1824 of the insert is disposed within the well 1816, to provide a secondary current supply electrically connected via the cable 1826 to electrical device(s) 1830 and/or 1832, e.g., one or more piezoelectric crystals in a stack coupled to a tip 1834 via a horn (see FIG. 4, e.g.), located on the distal portion 1822 of the insert 1820.

The system 1800 thus allows a standard, pre-existing magnetostrictive scaling unit (e.g., generator 1802, power supply 1804, water supply 1806, optional footswitch 1808, cable 1810, handpiece 1812, primary coil 1814, and/or well 1816), to be used to power and/or supply water via cable 1826 to a remotely located electrical device(s) 1830, 1832 in a distal portion 1822, which in some embodiments may incorporate the electrical and mechanical components from any one of FIGS. 1-17 and/or corresponding to any electrical device described herein. In some embodiments, the electrical device(s) 1830, 1832 may be for example, a piezoelectric crystal stack, temperature detector, density detector, strain detector, conductivity detector, power level detector, high speed rotary machine, low speed rotary machine, illumination light, curing light, spectroscopic detector, prophylactic dispenser, medicament dispenser, imaging device, operational controller, microprocessor, memory module, communication device, electromagnet, ac to dc converter, and combinations thereof. In one preferred embodiment, the distal portion 1822 is a piezo handpiece provided with a removable tip 1834 for dental scaling. In this manner the magnetostrictive scaling unit can be used to power either a conventional magnetostrictive insert/tip or a piezo handpiece and tip as desired. The piezo handpiece/tip in this embodiment is located remotely from the magnetostrictive handpiece 1812, tethered by the cable 1826, and is lighter relative to the embodiment where the piezo device is mechanically integrated with the proximal portion 1824 of the insert 1820. The handpiece 1812 may, for example, be clipped or otherwise secured permanently or temporarily to a structure such as a dental chair, table, or support structure, or even to a surface of the generator unit 1802 itself, sufficiently near the patient or other operating field to be reached upon extension of the cable 1826.

In an embodiment, a method of operating an ultrasonic handpiece comprising a primary coil disposed about a well and electrically connected to a primary current supply, comprises disposing an insert according to an embodiment of the instant disclosure into the well of the ultrasonic handpiece, wherein the insert comprising a secondary coil disposed about at least a portion of the insert dimensioned and arranged to be disposable within the well such that the secondary coil is inductively coupled to the primary coil, the secondary coil being in electrical communication with at least one electrical device, and supplying power to the primary coil via the primary current supply; and powering the at least one electrical device with the secondary coil via induction of the power from the primary coil into the secondary coil.

In an embodiment, a method of using a handheld electrical tool system comprising a generator electrically connected to a handpiece comprising a primary coil disposed about a well and an insert adapted to be received in the well of the handpiece, the method comprising placing a proximal portion of the insert in the well; activating the generator to provide a primary current supply to the primary coil; positioning a secondary coil wound on the proximal portion of the insert within the primary coil to induce a secondary current supply from the secondary coil without inducing magnetostrictive vibration of the proximal portion of the insert; and powering an electrical device located on a distal portion of the insert with the secondary current supply.

In an embodiment, a method of retrofitting a magnetostrictive ultrasonic handpiece comprising a primary coil disposed about a well and electrically connected to a magnetostrictive primary current supply comprises inserting an insert according to an embodiment of the instant disclosure into the well of the ultrasonic handpiece, the insert comprising a secondary coil disposed about at least a portion of the insert dimensioned and arranged to be disposable within the well such that the secondary coil is inductively coupled to the primary coil, the secondary coil in electrical communication with at least one electrical device powered by the secondary coil. In an embodiment, the electrical device comprises a piezoelectric stack mechanically coupled to a horn, the horn couple-able to a tip.

In an embodiment, a method of using a magnetostrictive ultrasonic dental scaler system for piezoelectric dental scaling, comprises removing a magnetostrictive ultrasonic insert from a well of a handpiece comprising a primary coil disposed about the well; connecting the handpiece to a generator to provide a primary power supply to the primary circuit, the generator enabled to provide the primary power supply having characteristics for operation of the magnetostrictive ultrasonic insert; placing in the well a proximal portion of an insert comprising a secondary coil; positioning the secondary coil within the primary coil to induce a secondary current supply from the secondary coil; and powering a piezoelectric stack located on a distal portion of the insert and mechanically coupled to a horn with the secondary current supply to ultrasonically vibrate a tip coupled to the horn.

Embodiments

Accordingly, the present invention provides the following embodiments of the invention:

A. A handheld electrical tool system, comprising:
   a handpiece comprising a primary coil disposed about a well and electrically connected to a primary current supply;
   an insert comprising a distal portion and a proximal portion, the proximal portion dimensioned and arranged to be removably disposed within the well;
   an electrical device located on the insert, wherein the electrical device is selected from the group consisting of: a piezoelectric crystal stack, caries detector, cancer detector, temperature detector, density detector, strain detector, conductivity detector, power level detector, high speed rotary machine, low speed rotary machine, illumination light, curing light, spectroscopic detector, prophylactic dispenser, medicament dispenser, imaging device, operational controller, microprocessor, memory module, communication device, an electromagnet, an ac to dc converter, and combinations thereof, with the proviso that if the proximal portion of the insert is magnetostrictively active the electrical device is not an illumination light;
   a secondary coil disposed about the proximal portion of the insert to inductively couple to the primary coil when the proximal portion of the insert is disposed within the well to provide a secondary current supply; and
   a circuit to electrically connect the electrical device to the secondary current supply.

B. A handheld electrical tool system, comprising:
   a handpiece comprising a primary coil disposed about a well and electrically connected to a primary current supply;
   an insert comprising a distal portion and a proximal portion, the proximal portion being magnetostrictively inactive and dimensioned and arranged to be removably disposed within the well;
   an electrical device located on the insert;
   a secondary coil disposed about and in contact with the proximal portion of the insert to inductively couple to the primary coil when the proximal portion of the insert is disposed within the well to provide a secondary current supply; and
   a circuit to electrically connect the electrical device to the secondary current supply.

C. The handheld electrical tool system according to Embodiment B, wherein the electrical device comprises one or more a piezoelectric crystal stack, caries detector, cancer detector, temperature detector, density detector, strain detector, conductivity detector, power level detector, high speed rotary machine, low speed rotary machine, illumination light, curing light, spectroscopic detector, prophylactic dispenser, medicament dispenser, imaging device, operational controller, microprocessor, memory module, communication device, an electromagnet, an ac to dc converter, or a combination thereof.

D. The handheld electrical tool system according to Embodiment A, B or C, wherein the proximal portion of the insert comprises a metallic core having a relative magnetic permeability of greater than 1 and wherein the secondary coil is disposed around the metallic core.

E. The handheld electrical tool system according to Embodiment A, B, C or D, wherein the electrical device comprises a piezoelectric stack mechanically coupled to a horn, and wherein the horn is releasably coupled to a tip.

F. The handheld electrical tool system according to Embodiment A, B, C, D, or E, further comprising an insert inventory comprising a plurality of the inserts for the handpiece, wherein the inserts are interchangeable in the handpiece and the electrical devices of the respective ones of the plurality of inserts are the same or different.

G. The handheld electrical tool system according to Embodiment A, B, C, D, E, or F, further comprising an insert inventory comprising a plurality of interchangeable inserts for the handpiece, wherein the inventory comprises at least the electrical device insert and an ultrasonic magnetostrictive insert, and a magnetostrictive power generator to provide the primary current with characteristics to selectively operate the ultrasonic magnetostrictive insert and the electrical device insert.

H. The handheld electrical tool system according to Embodiment A, B, C, D, E, F, or G, wherein the proximal portion of the insert comprises an ultrasonic magnetostrictive stack and wherein the secondary coil is disposed around and in contact with the magnetostrictive stack.

I. The handheld electrical tool system according to Embodiment A, B, C, D, E, F, G, or H, further comprising a water supply in fluid communication with the well, and a water flow passage from the well through the insert.

J. The handheld electrical tool system according to Embodiment A, B, C, D, E, F, G, H, or I, wherein the insert further comprises an operating characteristic controller enabled to control a value of an operating characteristic of the electrical device.

K. The handheld electrical tool system according to Embodiment A, B, C, D, E, F, G, H, I or J, wherein the operating characteristic controller is electrically connected to the secondary current supply.

L. The handheld electrical tool system according to Embodiment A, B, C, D, E, F, G, H, I, J, or K, further comprising a microprocessor coupled to the operating characteristic controller, the microprocessor comprising an algorithm to determine a desired value of the operating characteristic and to set the value of the operating characteristic of the electrical device to the desired value.

M. The handheld electrical tool system according to Embodiment A, B, C, D, E, F, G, H, I, J, K, or L, wherein the operating characteristic comprises a tip device profile corresponding to a tool attached to the insert, a proximity to one or more operating boundary parameters, a power level, a dental site temperature, a tool temperature, a dental hygiene material, a fluid type contained in a fluid supply, a safety feedback loop, an error circumstance, a pressure, a strain, or a combination thereof.

N. The handheld electrical tool system according to Embodiment A, B, C, D, E, F, G, H, I, J, K, L, or M, the proximal insert portion comprising three longitudinal members spaced laterally apart, wherein the secondary coil is wound around a central longitudinal member passing through the spaces between the central longitudinal member and opposing outer longitudinal members, wherein each of the longitudinal members has a relative magnetic permeability greater than 10.

O. The handheld electrical tool system according to Embodiment A, B, C, D, E, F, G, H, I, J, K, L, M, or N, further comprising a tertiary coil disposed within a grip located on the distal portion electrically connected to the secondary coil; and a quaternary coil disposed about and in contact with the distal portion inductively coupled to the tertiary coil to provide a tertiary current supply, and a circuit to electrically connect the electrical device to the tertiary current supply.

P. A method of using a handheld electrical tool system comprising a generator electrically connected to a handpiece comprising a primary coil disposed about a well and an insert adapted to be received in the well of the handpiece, comprising:
    placing a proximal portion of the insert in the well;
    activating the generator to provide a primary current supply to the primary coil;
    positioning a secondary coil wound on the proximal portion of the insert within the primary coil to induce a secondary current supply from the secondary coil without inducing magnetostrictive vibration of the proximal portion of the insert; and
    powering an electrical device located on a distal portion of the insert with the secondary current supply.

Q. The method according to Embodiment P, wherein the electrical device comprises one or more of a piezoelectric crystal stack, caries detector, cancer detector, temperature detector, density detector, strain detector, conductivity detector, power level detector, high speed rotary machine, low speed rotary machine, illumination light, curing light, spectroscopic detector, prophylactic dispenser, medicament dispenser, imaging device, operational controller, microprocessor, memory module, communication device, or a combination thereof.

R. The method according to Embodiment P or Q, wherein the secondary coil is disposed around at least a portion of a magnetostrictively inactive metallic core having a relative magnetic permeability of greater than 1.

S. The method according to Embodiment P, Q, or R, wherein the electrical device comprises a piezoelectric stack mechanically coupled to a horn, the horn coupled to a tip.

T. The method according to Embodiment P, Q, R, or S, further comprising:
    maintaining an insert inventory comprising a plurality of the inserts for the handpiece, wherein the inserts are interchangeable in the handpiece and the electrical devices of the respective ones of the plurality of inserts are the same or different; and
    selecting one of the plurality of inserts from the inventory for the placement in the handpiece.

U. The method according to Embodiment P, Q, R, S, or T, further comprising:
    selecting another one of the plurality of inserts from the inventory for placement in the handpiece;
    removing the one of the plurality of inserts from the handpiece and returning the removed insert to the inventory; and
    placing the selected other one of the plurality of inserts in the handpiece.

V. The method according to Embodiment P, Q, R, S, T, or U, further comprising:
    maintaining an insert inventory comprising a plurality of interchangeable inserts for the handpiece, wherein the inventory comprises at least the electrical device insert and an ultrasonic magnetostrictive insert; and
    connecting the handpiece to a magnetostrictive power generator to provide the primary current with characteristics to operate either of the ultrasonic magnetostrictive insert or the electrical device insert;
    selecting one of the plurality of inserts from the inventory;
    placing the selected one of the plurality of inserts the handpiece; and
    operating the insert placed in the handpiece with the magnetostrictive power generator.

W. The method according to Embodiment P, Q, R, S, T, U, or V, wherein the inventory comprises an ultrasonic magnetostrictive insert comprising the secondary coil disposed around a magnetostrictive stack.

X. The method according to Embodiment P, Q, R, S, T, U, V, or W, further comprising supplying water to the well, and flowing the water from the well through a water flow passage formed in the insert.

Y. The method according to Embodiment P, Q, R, S, T, U, V, W, or X, further comprising using an operating characteristic controller in the insert to control a value of an operating characteristic of the electrical device.

Z. The method according to Embodiment P, Q, R, S, T, U, V, W, X, or Y, further comprising inputting at least one control parameter into the operating characteristic controller.

A1. The method according to Embodiment P, Q, R, S, T, U, V, W, X, Y, or Z, wherein the operating characteristic or control parameter comprises: a tip device profile corresponding to a tool attached to the insert, a proximity to one or more operating boundary parameters, a power level, a dental site temperature, a tool temperature, a dental hygiene material, a fluid type contained in a fluid supply, a safety feedback loop, an error circumstance, a pressure, a strain, or a combination thereof.

B1. A method of using a magnetostrictive ultrasonic dental scaler system for piezoelectric dental scaling, comprising:
 removing a magnetostrictive ultrasonic insert from a well of a handpiece comprising a primary coil disposed about the well;
 connecting the handpiece to a generator to provide a primary power supply to the primary circuit, the generator enabled to provide the primary power supply having characteristics for operation of the magnetostrictive ultrasonic insert;
 placing in the well a proximal portion of an insert comprising a secondary coil;
 positioning the secondary coil within the primary coil to induce a secondary current supply from the secondary coil; and
 powering a piezoelectric stack located on a distal portion of the insert and mechanically coupled to a horn with the secondary current supply to ultrasonically vibrate a tip coupled to the horn. The foregoing disclosure and description of the invention is illustrative and explanatory thereof and it can be readily appreciated by those skilled in the art that various changes in the size, shape and materials, as well as in the details of the illustrated construction or combinations of the elements described herein can be made without departing from the spirit of the invention.

C1. The handheld electrical tool system according to Embodiment A, B, C, D, E, F, G, H, I, J, K, L, M, N, or O, wherein a proximal portion of the insert carrying the secondary coil is disposable in the well and connected via a cable to a distal portion of the insert carrying the electrical device powered by the secondary coil.

D1. The method according to Embodiment P, Q, R, S, T, U, V, W, X, Y, Z, A1, or B1, wherein a proximal portion of the insert carrying the secondary coil is disposable in the well and connected via a cable to a distal portion of the insert carrying the electrical device powered by the secondary coil.

While the invention has been illustrated and described in detail in the drawings and foregoing description, the same is to be considered as illustrative and not restrictive in character, it being understood that only some embodiments have been shown and described and that all changes and modifications that come within the spirit of the inventions are desired to be protected. It should be understood that while the use of words such as preferable, preferably, preferred, more preferred or exemplary utilized in the description above indicate that the feature so described may be more desirable or characteristic, nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A handheld electrical tool system, comprising:
 a handpiece comprising a primary coil disposed about a well and electrically connected to a primary current supply;
 an insert comprising a distal portion and a proximal portion, the proximal portion being magnetostrictively inactive and dimensioned and arranged to be removably disposed within the well;
 an electrical device located on the distal portion of the insert;
 a secondary coil wound on the magnetostrictively inactive proximal portion of the insert to position the secondary coil within the primary coil and inductively couple the secondary coil to the primary coil when the proximal portion of the insert is disposed within the well to provide a secondary current supply without inducing magnetostrictive vibration; and
 a circuit to electrically connect the electrical device to the secondary current supply.

2. The handheld electrical tool system of claim 1, further comprising a cable tethering the distal portion of the insert to the proximal portion of the insert.

3. The handheld electrical tool system of claim 1, wherein the electrical device comprises one or more of a piezoelectric crystal stack, illumination light, curing light, or a combination thereof.

4. The handheld electrical tool system of claim 1, wherein the proximal portion of the insert comprises a metallic core having a relative magnetic permeability of greater than 1 and wherein the secondary coil is disposed around the metallic core.

5. The handheld electrical tool system of claim 1, wherein the electrical device comprises a piezoelectric stack mechanically coupled to a horn, and wherein the horn is releasably coupled to a tip.

6. The handheld electrical tool system of claim 1, further comprising a water supply in fluid communication with the well, and a water flow passage from the well through the insert.

7. The handheld electrical tool system of claim 1, the proximal insert portion comprising three longitudinal members spaced laterally apart, wherein the secondary coil is wound around a central longitudinal member passing through the spaces between the central longitudinal member and opposing outer longitudinal members, wherein each of the longitudinal members has a relative magnetic permeability greater than 10.

8. A method of using a handheld electrical tool system comprising a generator electrically connected to a handpiece comprising a primary coil disposed about a well and an electrical device insert adapted to be received in the well of the handpiece, comprising:
 placing a proximal portion of the electrical device insert in the well, wherein the proximal portion of the electrical device insert placed in the well is magnetostrictively inactive;
 activating the generator to provide a primary current supply to the primary coil;
 positioning a secondary coil wound on the proximal portion of the electrical device insert within the primary coil to induce a secondary current supply from the secondary coil without inducing magnetostrictive vibration of the proximal portion of the electrical device insert; and
 powering an electrical device located on a distal portion of the electrical device insert with the secondary current supply.

9. The method of claim 8, further comprising conducting the secondary current through a cable tethering the proximal portion of the insert to the distal portion of the insert.

10. The method of claim 8, wherein the electrical device comprises one or more of a piezoelectric crystal stack, illumination light, curing light, or a combination thereof.

11. The method of claim 8, wherein the proximal portion of the insert comprises a magnetostrictively inactive metallic core having a relative magnetic permeability of greater than 1 and wherein the secondary coil is disposed around at least a portion of the magnetostrictively inactive metallic core.

12. The method of claim 8, wherein the electrical device comprises a piezoelectric stack mechanically coupled to a horn, the horn coupled to a tip.

13. The method of claim 8, further comprising:
   maintaining an insert inventory comprising a plurality of interchangeable inserts for the handpiece, wherein the inventory of interchangeable inserts comprises at least the electrical device insert and an ultrasonic magnetostrictive insert;
   connecting the handpiece to a magnetostrictive power generator to provide the primary current with characteristics to operate either of the ultrasonic magnetostrictive insert or the electrical device insert;
   selecting one of the interchangeable inserts from the inventory;
   placing the selected one of the interchangeable inserts in the handpiece; and
   operating the interchangeable insert placed in the handpiece with the magnetostrictive power generator.

14. The method of claim 13, further comprising conducting the secondary current through a cable tethering the proximal portion of the insert to the distal portion of the insert.

15. The method of claim 8, wherein the proximal portion of the insert comprises three longitudinal members spaced laterally apart, wherein the secondary coil is wound around a central longitudinal member passing through the spaces between the central longitudinal member and opposing outer longitudinal members, wherein each of the longitudinal members has a relative magnetic permeability greater than 10.

16. A handheld electrical tool system comprising:
   a handpiece comprising a primary coil disposed about a well and electrically connected to a primary current supply;
   an insert inventory comprising a plurality of interchangeable inserts for the handpiece, wherein the inventory comprises at least an ultrasonic magnetostrictive insert and a piezoelectric insert,
   wherein the piezoelectric insert comprises:
      a distal portion and a proximal portion, the proximal portion being magnetostrictively inactive and dimensioned and arranged to be removably disposed within the well;
      an electrical device located on the distal portion of the piezoelectric insert, wherein the electrical device comprises a piezoelectric crystal stack in the distal portion of the insert;
      a secondary coil wound on the magnetostrictively inactive proximal portion of the piezoelectric insert to position the secondary coil within the primary coil and inductively couple the secondary coil to the primary coil when the proximal portion of the piezoelectric insert is disposed within the well to provide a secondary current supply without inducing magnetostrictive vibration; and
      a circuit to electrically connect the electrical device to the secondary current supply.

17. The handheld electrical tool system of claim 16, further comprising a cable tethering the distal portion of the piezoelectric insert to the proximal portion of the piezoelectric insert.

* * * * *